US012582971B2

(12) United States Patent
Xiong et al.

(10) Patent No.: US 12,582,971 B2
(45) Date of Patent: Mar. 24, 2026

(54) COMPOSITE OXIDE CATALYST, PREPARATION METHOD THEREFOR, AND USE THEREOF

(71) Applicant: Shanghai Huayi New Material Co., Ltd, Shanghai (CN)

(72) Inventors: Desheng Xiong, Shanghai (CN); Yan Zhuang, Shanghai (CN); Yao Cui, Shanghai (CN); Xiaodong Chu, Shanghai (CN)

(73) Assignee: Shanghai Huayi New Material Co., Ltd, Shanghai (CN)

( * ) Notice: Subject to any disclaimer, the term of this patent is extended or adjusted under 35 U.S.C. 154(b) by 511 days.

(21) Appl. No.: 18/270,130

(22) PCT Filed: Nov. 2, 2021

(86) PCT No.: PCT/CN2021/128082
§ 371 (c)(1),
(2) Date: Jun. 28, 2023

(87) PCT Pub. No.: WO2022/142708
PCT Pub. Date: Jul. 7, 2022

(65) Prior Publication Data
US 2024/0066507 A1    Feb. 29, 2024

(30) Foreign Application Priority Data

Dec. 29, 2020    (CN) .......................... 202011588637.9

(51) Int. Cl.
| | |
|---|---|
| *C07C 45/38* | (2006.01) |
| *B01J 27/19* | (2006.01) |
| *B01J 37/00* | (2006.01) |
| *B01J 37/03* | (2006.01) |
| *B01J 37/08* | (2006.01) |

(52) U.S. Cl.
CPC ........... *B01J 27/19* (2013.01); *B01J 37/0036* (2013.01); *B01J 37/031* (2013.01); *B01J 37/088* (2013.01); *C07C 45/38* (2013.01)

(58) Field of Classification Search
CPC .. C07C 45/38; B01J 27/19; B01J 37/08; B01J 37/031
See application file for complete search history.

(56) References Cited

U.S. PATENT DOCUMENTS

| | | | |
|---|---|---|---|
| 4,101,448 A | 7/1978 | Shaw et al. | |
| 5,245,083 A | 9/1993 | Matsuura | |
| 7,803,972 B2 | 9/2010 | Gückel et al. | |
| 9,744,524 B2 * | 8/2017 | Xiong ...................... | B01J 37/04 |
| 2014/0024861 A1 | 1/2014 | Okumura et al. | |

FOREIGN PATENT DOCUMENTS

| | | |
|---|---|---|
| CN | 101340975 A | 1/2009 |
| CN | 103648641 A | 3/2014 |
| CN | 103933998 A | 7/2014 |
| CN | 106693981 A | 5/2017 |
| CN | 109012682 A | 12/2018 |
| CN | 112604701 A | 4/2021 |
| EP | 2213370 A2 | 8/2010 |
| WO | 2015004446 A1 | 1/2015 |

OTHER PUBLICATIONS

PCT International Search Report and Written Opinion, PCT/CN2021/128082, Jan. 29, 2022, 13 pages.
The State Intellectual Property Office of People's Republic of China, First Office Action and Search Report, Application No. 202011588637.9, Jan. 11, 2022, 9 pages.
The State Intellectual Property Office of People's Republic of China, Supplementary Search, Application No. 202011588637.9, Mar. 23, 2022, 1 page.
European Patent Office, Extended European Search Report, Application No. 21913452.5, Nov. 25, 2024, 6 pages.

* cited by examiner

*Primary Examiner* — Sikarl A Witherspoon
(74) *Attorney, Agent, or Firm* — Quarles & Brady LLP

(57) ABSTRACT

In a composite oxide catalyst, a preparation method therefor, and a use thereof, the catalyst has the following general formula: $MoFe_aAl_bP_cO_x$, wherein a=0.25-0.5, b=0.001-0.2, c=0.001-0.6, and x is a number satisfying the valence of the general formula. The catalyst has excellent low-temperature performance and thus has a long service life.

13 Claims, No Drawings

COMPOSITE OXIDE CATALYST, PREPARATION METHOD THEREFOR, AND USE THEREOF

CROSS-REFERENCE TO RELATED APPLICATION

This application represents the U.S. national stage entry of International Application No. PCT/CN2021/128082 filed Nov. 2, 2021, which claims priority to Chinese Application No. 202011588637.9 filed Dec. 29, 2020, the disclosure of which is incorporated herein by reference in its entirety and for all purposes.

BACKGROUND ART

Formaldehyde is an important basic raw material in the organic chemical industry, mainly produced by selective catalytic oxidation of methanol. The mainstream catalysts are electrolytic silver catalysts and iron molybdate composite oxide catalysts.

An electrolytic silver catalyst is generally a silver screen or a thin layer of silver particles. The process is simple with low investment. An excessive amount of methanol is used during the reaction, and the reaction temperature is about 600-720° C. However, the process has such problems as low methanol conversion, low formaldehyde selectivity, and short silver catalyst life.

The iron-molybdenum process employs an iron molybdate composite oxide catalyst. During the reaction, methanol is mixed with an excessive amount of air and reacted at a temperature of 260-400° C. The reaction temperature is lower than that of the silver process; the formaldehyde selectivity is higher than that of the silver process; and the catalyst life is also longer. This process is more powerful in production because it can also produce highly concentrated formaldehyde. Therefore, nowadays, most of the newly-built plants for production of formaldehyde by methanol oxidation adopt the iron-molybdenum process.

At present, the catalysts used in the iron-molybdenum process still have some problems, such as low catalyst activity. The process of methanol oxidation to formaldehyde requires the methanol conversion to be greater than 98.5%. In order to achieve a high conversion, the catalyst usually needs to participate in the reaction at a high temperature. However, the higher the reaction temperature, the easier it is for the molybdenum in the iron molybdate catalyst to sublime and run off. The run-off of molybdenum will in turn cause further decline in catalyst activity. The reaction temperature needs to be continuously raised to ensure that the methanol conversion is greater than 98.5%. Therefore, it is necessary to develop a catalyst having better activity and stability. For this reason, a number of modified catalysts have been proposed in the prior art.

CN 1100667 discloses a four-component catalyst of iron, molybdenum, cobalt and chromium, wherein the calcination temperature of the catalyst is 400° C., and the temperature of the methanol oxidation reaction is 340-380° C. CN1546232 discloses a four-component catalyst of iron, molybdenum, vanadium and chromium, wherein the temperature of the catalytic reaction is 350-365° C. The temperature of the methanol oxidation reaction using the iron-molybdenum catalyst disclosed by CN103933998 is 320-380° C. CN106693981 discloses a catalyst consisting of molybdenum, iron, vanadium, a promoter metal and a binder metal, wherein the promoter metal is one of nickel, aluminum, lanthanum, cerium, bismuth or manganese, and the binder metal is one of titanium or zirconium. The catalyst exhibits good activity at 280-300° C.

Although a desired methanol conversion can be achieved with each of the above-mentioned catalysts, the reaction temperatures experienced by these catalysts are rather high. In addition, the formaldehyde selectivity is not high enough, and there are a good number of by-products. The high reaction temperatures are harmful to the stability of the catalysts. When the activity of the catalysts is not maintained sufficiently, the service life of the catalysts will be shortened.

CN109012682A discloses a method for preparing an iron-molybdenum catalyst for methanol oxidation to formaldehyde, comprising: blending molybdenum:iron:metal promoter salt uniformly at a molar ratio of 1:0.2 to 0.67:0.01 to 0.2 by ball milling, followed by firing, wherein the metal promoter salt is selected from a soluble salt of a metal selected from cerium, vanadium, cobalt, nickel, barium, aluminum, chromium, titanium, manganese, zirconium and lanthanum, or a mixture of more than one soluble salts thereof. Although it turns out that the reaction efficiency is improved at a temperature of 285° C., the low temperature performance leaves room for further improvement.

Therefore, there is still a need in the art to find a catalyst with improved low-temperature performance and thus improved catalyst life for methanol oxidation to formaldehyde.

SUMMARY

One object of the present invention is to provide a catalyst for catalytic selective oxidation of methanol to formaldehyde with low reaction temperature and steady activity.

Another object of the present invention is to provide a method for preparing the catalyst of the present invention.

Therefore, one aspect of the present invention is directed to a catalyst for selective oxidation of methanol to formaldehyde, which has the following general formula:

$$MoFe_aAl_bP_cO_x$$

wherein a=0.25-0.5, b=0.001-0.2, c=0.001-0.6, and x is a number balancing the valence of the general formula.

Another aspect of the present invention is directed to a method for preparing a catalyst for selective oxidation of methanol to formaldehyde, wherein the catalyst has following general formula:

$$MoFe_aAl_bP_cO_x$$

wherein a=0.25-0.5, b=0.001-0.2, c=0.001-0.6, and x is a number balancing the valence of the general formula;

wherein the method comprises:

(1) providing an aqueous solution of a molybdenum salt with a molybdenum metal ion concentration of 0.1-2M in a stoichiometric amount;

(2) formulating stoichiometric amounts of an iron salt, an aluminum salt and phosphoric acid into an aqueous solution with a total metal ion concentration of 0.1-5M;

(3) mixing the above two solutions at 40-80° C. to obtain a slurry;

(4) aging and drying the slurry, mixing with a solid lubricant and water, and then tabletting; and (5) calcination.

Still another aspect of the present invention is directed to use of a catalyst in selective oxidation of methanol to formaldehyde, wherein the catalyst has following general formula:

$$MoFe_aAl_bP_cO_x$$

wherein a=0.25-0.5, b=0.001-0.2, c=0.001-0.6, and x is a number balancing the valence of the general formula.

DETAILED DESCRIPTION

The catalyst for selective oxidation of methanol to formaldehyde according to the present invention has the following general formula:

$$MoFe_aAl_bP_cO_x$$

wherein:

a=0.25-0.5, preferably 0.28-0.47, more preferably 0.31-0.44, desirably 0.34-0.41, most preferably 0.36-0.38;

b=0.001-0.2, preferably 0.003-0.018, more preferably 0.005-0.016, desirably 0.008-0.014, most preferably 0.01-0.012;

c=0.001-0.6, preferably 0.005-0.5, more preferably 0.01-0.4, desirably 0.015-0.3, most preferably 0.02-0.2;

x is a number balancing the valence of the general formula.

In an embodiment of the present invention, the catalyst is selected from $MoFe_{0.4}Al_{0.1}P_{0.3}O_x$, $MoFe_{0.35}Al_{0.05}P_{0.15}O_x$, $MoFe_{0.32}Al_{0.01}P_{0.03}O_x$, $MoFe_{0.33}Al_{0.14}P_{0.40}O_x$, $MoFe_{0.42}Al_{0.1}P_{0.1}O_x$, $MoFe_{0.31}Al_{0.006}P_{0.006}O_x$, $MoFe_{0.40}Al_{0.05}P_{0.1}O_x$, or a mixture of two or more thereof.

The method for preparing the catalyst of the present invention comprises the following steps:

(1) An aqueous solution of a molybdenum salt with a molybdenum metal ion concentration of 0.1-2M is provided in a stoichiometric amount.

The molybdenum salt suitable for the method of the present invention is not particularly limited, and may be selected from those known in the art. For example, a conventional soluble molybdenum salt may be used to formulate an aqueous solution. In an embodiment of the present invention, the soluble molybdenum salt includes hexaammonium molybdate.

The concentration of the formulated molybdenum salt aqueous solution is 0.1-2M, preferably 0.2-1.8M, more preferably 0.4-1.6M, desirably 0.6-1.4M, most preferably 0.8-1.2M.

The amount of molybdenum element in the molybdenum salt aqueous solution satisfies the required chemical composition of the final catalyst.

(2) Stoichiometric amounts of an iron salt, an aluminum salt and phosphoric acid are formulated into a solution with a total metal ion concentration of 0.1-5M.

In the present invention, the terms "metal", "metal ion" and "metal element" include phosphorus element. That is, in the description of the present invention, phosphorus element is viewed as a metal element.

The iron salt and aluminum salt suitable for the method of the present invention are not particularly limited, as long as they can form an aqueous solution. In an embodiment of the present invention, a soluble iron salt and/or a soluble aluminum salt are used to form an aqueous solution.

In an embodiment of the present invention, the soluble iron salt includes iron nitrate, and the soluble aluminum salt includes aluminum nitrate.

In the solution according to the present invention, the amounts of iron, aluminum and phosphorus elements satisfy the stoichiometric amounts required by the general formula of the catalyst, and the concentration of the metal ions consisting of iron element, aluminum element and phosphorus element is 0.1-5M, preferably 0.4-4.6M, more preferably 0.8-4.2M, desirably 1.2-3.8M, most preferably 1.6-3.2M.

(3) The above two solutions are mixed at 40-80° C. to obtain a slurry.

The method for mixing the molybdenum solution with the solution containing iron, aluminum and phosphoric acid is not particularly limited. The former may be added to the latter, or the latter may be added to the former.

In an embodiment of the present invention, the solution containing iron, aluminum and phosphoric acid formulated in step (2) is slowly added to the molybdenum solution formulated in step (1) to carry out precipitation reaction.

In an embodiment of the present invention, the precipitation reaction time is 30-120 minutes, preferably 40-110 minutes, more preferably 50-100 minutes, desirably 60-90 minutes, most preferably 70-80 minutes.

The above two solutions are mixed at a temperature of 40-80° C., preferably 45-75° C., more preferably 50-70° C., desirably 55-65° C., most preferably 58-62° C.

(4) The slurry is aged, dried, mixed with a solid lubricant and water, and then tabletting was performed.

The method for aging the slurry suitable for the present invention is not particularly limited, and may be a conventional aging method known in the art. In an embodiment of the present invention, the slurry is aged for 1-4 hours, preferably aged for 1.5-3.5 hours, more preferably aged for 2-3 hours.

After aging the slurry, the method of the present invention comprises a drying step. The applicable drying method is not particularly limited, and may be a conventional drying method known in the art. In an embodiment of the present invention, the slurry is dried at a temperature of 110-200° C., preferably at a temperature of 120-190° C., more preferably at a temperature of 120-180° C., desirably at a temperature of 130-170° C., most preferably at a temperature of 140-160° C. for 8-24 hours, preferably 10-22 hours, more preferably 12-20 hours, desirably 14-18 hours, most preferably 15-17 hours.

In an embodiment of the present invention, the method of the present invention further comprises a step of pulverizing the dried product (i.e., a catalyst precursor) after drying. Since the purpose of pulverization is to facilitate mixing in a subsequent step, the degree of pulverization is not particularly limited, as long as it is conducive to speeding up subsequent uniform mixing with water and the solid lubricant. In an embodiment of the present invention, the catalyst precursor is pulverized to less than 180 mesh, preferably less than 190 mesh, more preferably less than 200 mesh.

The solid lubricant suitable for the method of the present invention is not particularly limited, and may be a conventional solid lubricant known in the art. In an embodiment of the present invention, the solid lubricant is selected from graphite, stearic acid or a mixture thereof.

In the method of the present invention, the purpose of adding the solid lubricant and water is to facilitate molding the catalyst precursor powder. Hence, those of ordinary skill in the art can easily determine an appropriate amount after reading the disclosure of the present invention.

The tabletting method suitable for the method of the present invention is not particularly limited, and may be a conventional tabletting method known in the art.

(5) Calcination is performed.

It is a conventional means in the art to calcine the tableted catalyst precursor. In an embodiment of the present invention, the molded catalyst precursor is calcined at a temperature of 350° C.-500° C., preferably 380-470° C., more preferably 400-450° C., most preferably 420-440° C. for 2-12 hours, preferably 3-11 hours, more preferably 4-10 hours, most preferably 6-8 hours.

In an embodiment of the present invention, the steps for manufacturing the catalyst of the present invention include: dissolving hexaammonium molybdate in water in a stoichiometric amount to formulate solution A; dissolving ferric nitrate nonahydrate in water, then slowly adding aluminum nitrate nonahydrate, and after complete dissolution, adding phosphoric acid to obtain solution B; slowly adding B dropwise to A at 40-80° C. for 40-90 minutes under stirring; after complete addition of solution B, keeping stirring the slurry at 40-90° C. for 1-4 hours for aging, and then drying at 110-180° C. for 8-18 hours; pulverizing the dried material, then adding the solid lubricant and water to mix uniformly, and then tabletting; calcining the tableted sample at a temperature of 250-500° C. for 2-8 hours to obtain the catalyst.

The catalyst of the present invention is suitable for use as a catalyst for oxidation of methanol to formaldehyde. The method suitable for using the catalyst of the present invention to catalyze oxidation of methanol to formaldehyde is not particularly limited, and may be a conventional method known in the art, except that the catalyst of the present invention can implement catalytic oxidation at a lower temperature to achieve the same catalytic effect as the prior art.

In an embodiment of the present invention, the catalytic reaction of the present invention comprises the following steps:

The selective oxidation reaction of methanol is conducted in a fixed-bed reaction apparatus. A methanol liquid is vaporized and mixed with air and nitrogen to form a reaction gas. The reaction gas comprises 5-15 mol % methanol, preferably 8-12 mol % methanol, and 8-15 mol % oxygen. The space velocity of the reaction gas is 6000-15000 $h^{-1}$, preferably 8000-12000 $h^{-1}$, and the reaction temperature is 220-400° C., preferably 260-360° C. The reaction pressure is ambient pressure.

Compared with the prior art, the present invention improves the activity and stability of the catalyst through optimization of the catalyst components. The catalyst can provide a methanol conversion of 98.5% at a relatively low reaction temperature. The activity of the catalyst decreases very slowly in a long running cycle. The activity of the catalyst is stable.

The present invention will be further illustrated with reference to the following Examples.

Example 1

1. Preparation of Catalyst 88.276 grams of hexaammonium molybdate was dissolved in 500 grams of pure water to formulate solution A. 80.80 grams of ferric nitrate nonahydrate was dissolved in 400 grams of water, and then 18.76 grams of aluminum nitrate nonahydrate was added slowly. After complete dissolution, 17.71 grams of 83% phosphoric acid was added to obtain solution B. Solution B was added dropwise to solution A slowly at 50° C. for 60 minutes under stirring. After the dropwise addition of solution B was completed, the resulting slurry was continued to be stirred at 60° C. for 2 hours for aging, and then dried at 130° C. for 10 hours. The dried material was pulverized to less than 200 mesh. Then, 2 grams of graphite and 8 grams of pure water were added and mixed uniformly, and then tabletting was performed. The tabletted sample was calcined at 450° C. for 4 h to obtain a catalyst. The molar ratio of the catalyst components Mo:Fe:Al:P was 1:0.4:0.1:0.3.

6

2. Evaluation on Catalyst Activity

The oxidation reaction of methanol was conducted in a fixed-bed reaction apparatus, and the catalyst was fixed in a stainless steel reaction tube with an inner diameter of 10 mm. Before the test, the catalyst obtained by calcinations was ground and sieved to obtain 40-60 mesh particles, and then fixed in the reaction tube.

Methanol was metered using a duplex plunger pump, and air and nitrogen were metered using mass flow meters. After the methanol liquid was vaporized with a vaporizer, it was mixed with nitrogen and air, and then entered the catalyst bed for reaction. The reaction gas contained 11 mol % methanol, 10 mol % oxygen, and a balance of nitrogen. The space velocity of the reaction gas was 12000 $h^{-1}$. After feeding the reaction gas for 2 hours, a gas sample was taken and analyzed with gas chromatography to determine the contents of methanol, dimethyl ether, CO and $CO_2$. The conversion of methanol and the selectivity of dimethyl ether, CO and $CO_2$ were calculated from the test results of gas chromatography. Calculations were performed according to the following equations:

Methanol conversion: $C_{methanol}$=(amount of charged methanol−amount of discharged methanol)/amount of charged methanol Dimethyl ether selectivity: $S_{dimethyl\ ether}$=2×amount of discharged dimethyl ether/(amount of charged methanol×methanol conversion)

CO selectivity: $S_{CO}$=amount of discharged CO/(amount of charged methanol×methanol conversion)

$CO_2$ selectivity: $S_{CO2}$=amount of discharged $CO_2$/(amount of charged methanol×methanol conversion)

Formaldehyde selectivity: $S_{formaldehyde}$=1−$S_{dimethyl\ ether}$−$S_{CO}$−$S_{CO2}$ The temperature of the reactor was adjusted until the methanol conversion reached 98.5%. The methanol conversion reached 98.5% when the catalyst of this Example was used in the reaction at 235° C., and the formaldehyde selectivity was 96.0%. In order to test the stability of the catalyst, the reaction was continued at 235° C., and samples were taken and analyzed regularly. After 240 hours of reaction, the methanol conversion was 98.0%, and the formaldehyde selectivity was 96.2%. As shown by the experimental results, after 240 hours of reaction, the methanol conversion only decreased by 0.5%, and the formaldehyde selectivity increased by 0.2%, indicating good stability of the catalyst. The results are listed in Table 1.

Example 2

1. Preparation of Catalyst 88.276 grams of hexaammonium molybdate was dissolved in 500 grams of pure water to formulate solution A. 70.70 grams of ferric nitrate nonahydrate was dissolved in 400 grams of water, and then 9.38 grams of aluminum nitrate nonahydrate was added slowly. After complete dissolution, 10.1 grams of 83% phosphoric acid was added to obtain solution B. Solution B was added dropwise to solution A slowly at 50° C. for 60 minutes under stirring. After the dropwise addition of solution B was completed, the resulting slurry was continued to be stirred at 60° C. for 2 hours for aging, and then dried at 130° C. for 10 hours. The dried material was pulverized to less than 200 mesh. Then, 2 grams of graphite and 8 grams of pure water were added and mixed uniformly, and then tabletting was performed. The tabletted sample was calcined at 480° C. for 3 h to obtain a catalyst. The molar ratio of the catalyst components Mo:Fe:Al:P was 1:0.35:0.05:0.15.

2. Evaluation on Catalyst Activity

The activity and stability of the catalyst were tested in the same manner as in Example 1.

When the catalyst was used in the reaction at 242° C., the methanol conversion reached 98.5%, and the formaldehyde selectivity was 96.3%. After 240 hours of reaction, the methanol conversion was 98.2%, and the formaldehyde selectivity was 96.2%. The results are listed in Table 1.

Example 3

1. Preparation of Catalyst 88.276 grams of hexaammonium molybdate was dissolved in 500 grams of pure water to formulate solution A. 64.64 grams of ferric nitrate nonahydrate was dissolved in 400 grams of water, and then 1.88 grams of aluminum nitrate nonahydrate was added slowly. After complete dissolution, 1.77 grams of 83% phosphoric acid was added to obtain solution B. Solution B was added dropwise to solution A slowly at 50° C. for 60 minutes under stirring. After the dropwise addition of solution B was completed, the resulting slurry was continued to be stirred at 80° C. for 5 hours for aging, and then dried at 150° C. for 10 hours. The dried material was pulverized to less than 200 mesh. Then, 2 grams of stearic acid and 10 grams of pure water were added and mixed uniformly, and then tabletting was performed. The tabletted sample was calcined at 460° C. for 6 h to obtain a catalyst. The molar ratio of the catalyst components Mo:Fe:Al:P was 1:0.32:0.01:0.03.

2. Evaluation on Catalyst Activity

The activity and stability of the catalyst were tested in the same manner as in Example 1.

When the catalyst was used in the reaction at 255° C., the methanol conversion reached 98.5%, and the formaldehyde selectivity was 96.5%. After 240 hours of reaction, the methanol conversion was 97.8%, and the formaldehyde selectivity was 96.0%. The results are listed in Table 1.

Example 4

1. Preparation of Catalyst 88.276 grams of hexaammonium molybdate was dissolved in 500 grams of pure water to formulate solution A. 66.66 grams of ferric nitrate nonahydrate was dissolved in 400 grams of water, and then 26.26 grams of aluminum nitrate nonahydrate was added slowly. After complete dissolution, 23.61 grams of 83% phosphoric acid was added to obtain solution B. Solution B was added dropwise to solution A slowly at 60° C. for 30 minutes under stirring. After the dropwise addition of solution B was completed, the resulting slurry was continued to be stirred at 60° C. for 3 hours for aging, and then dried at 140° C. for 24 hours. The dried material was pulverized to less than 200 mesh. Then, 2 grams of stearic acid and 20 grams of pure water were added and mixed uniformly, and then tabletting was performed. The tabletted sample was calcined at 460° C. for 6 h to obtain a catalyst. The molar ratio of the catalyst components Mo:Fe:Al:P was 1:0.33:0.14:0.40.

2. Evaluation on Catalyst Activity

The activity and stability of the catalyst were tested in the same manner as in Example 1.

When the catalyst was used in the reaction at 230° C., the methanol conversion reached 98.5%, and the formaldehyde selectivity was 95.2%. After 240 hours of reaction, the methanol conversion was 98.3%, and the formaldehyde selectivity was 95.0%. The results are listed in Table 1.

Example 5

1. Preparation of Catalyst 88.28 grams of hexaammonium molybdate was dissolved in 500 grams of pure water to formulate solution A. 84.84 grams of ferric nitrate nonahydrate was dissolved in 400 grams of water, and then 18.76 grams of aluminum nitrate nonahydrate was added slowly. After complete dissolution, 5.90 grams of 83% phosphoric acid was added to obtain solution B. Solution B was added dropwise to solution A slowly at 60° C. for 30 minutes under stirring. After the dropwise addition of solution B was completed, the resulting slurry was continued to be stirred at 80° C. for 2 hours for aging, and then dried at 150° C. for 12 hours. The dried material was pulverized to less than 200 mesh. Then, 2 grams of graphite and 10 grams of pure water were added and mixed uniformly, and then tabletting was performed. The tabletted sample was calcined at 450° C. for 4 h to obtain a catalyst. The molar ratio of the catalyst components Mo:Fe:Al:P was 1:0.42:0.10:0.10.

2. Evaluation on Catalyst Activity

The activity and stability of the catalyst were tested in the same manner as in Example 1.

When the catalyst was used in the reaction at 232° C., the methanol conversion reached 98.5%, and the formaldehyde selectivity was 96.8%. After 240 hours of reaction, the methanol conversion was 98.1%, and the formaldehyde selectivity was 96.5%. The results are listed in Table 1.

Example 6

1. Preparation of Catalyst 88.28 grams of hexaammonium molybdate was dissolved in 500 grams of pure water to formulate solution A. 62.62 grams of ferric nitrate nonahydrate was dissolved in 400 grams of water, and then 1.13 grams of aluminum nitrate nonahydrate was added slowly. After complete dissolution, 0.35 grams of 83% phosphoric acid was added to obtain solution B. Solution B was added dropwise to solution A slowly at 60° C. for 30 minutes under stirring. After the dropwise addition of solution B was completed, the resulting slurry was continued to be stirred at 80° C. for 2 hours for aging, and then dried at 150° C. for 12 hours. The dried material was pulverized to less than 200 mesh. Then, 2 grams of graphite and 10 grams of pure water were added and mixed uniformly, and then tabletting was performed. The tabletted sample was calcined at 450° C. for 4 h to obtain a catalyst. The molar ratio of the catalyst components Mo:Fe:Al:P was 1:0.31:0.006:0.006.

2. Evaluation on Catalyst Activity

The activity and stability of the catalyst were tested in the same manner as in Example 1.

When the catalyst was used in the reaction at 261° C., the methanol conversion reached 98.5%, and the formaldehyde selectivity was 95.1%. After 240 hours of reaction, the methanol conversion was 95.3%, and the formaldehyde selectivity was 95.5%. The results are listed in Table 1.

Example 7

1. Preparation of Catalyst 88.28 grams of hexaammonium molybdate was dissolved in 500 grams of pure water to formulate solution A. 80.80 grams of ferric nitrate nonahydrate was dissolved in 400 grams of water, and then 9.38 grams of aluminum nitrate nonahydrate was added slowly. After complete dissolution, 5.90 grams of 83% phosphoric acid was added to obtain solution B. Solution B was added dropwise to solution A slowly at 60° C. for 30 minutes under stirring. After the dropwise addition of solution B was completed, the resulting slurry was continued to be stirred at 80° C. for 2 hours for aging, and then dried at 150° C. for 12 hours. The dried material was pulverized to less than 200 mesh. Then, 2 grams of graphite and 10 grams of pure water were added and mixed uniformly, and then tabletting was performed. The tabletted sample was calcined at 420° C. for 6 h to obtain a catalyst. The molar ratio of the catalyst components Mo:Fe:Al:P was 1:0.40:0.05:0.10.

2. Evaluation on Catalyst Activity

The activity and stability of the catalyst were tested in the same manner as in Example 1.

When the catalyst was used in the reaction at 261° C., the methanol conversion reached 98.5%, and the formaldehyde selectivity was 96.6%. After 240 hours of reaction, the methanol conversion was 97.9%, and the formaldehyde selectivity was 97.0%. The results are listed in Table 1.

Comparative Example 1

1. Preparation of Catalyst

The method for preparing the catalyst is similar to Example 1, except that aluminum nitrate and phosphoric acid were not added:

88.28 grams of hexaammonium molybdate was dissolved in 500 grams of pure water to formulate solution A. 80.80 grams of ferric nitrate nonahydrate was dissolved in 400 grams of water to obtain solution B. Solution B was added dropwise to solution A slowly at 60° C. for 30 minutes under stirring. After the dropwise addition of solution B was completed, the resulting slurry was continued to be stirred at 80° C. for 2 hours for aging, and then dried at 150° C. for 12 hours. The dried material was pulverized to less than 200 mesh. Then, 2 grams of graphite and 10 grams of pure water were added and mixed uniformly, and then tabletting was performed. The tabletted sample was calcined at 450° C. for 6 h to obtain a catalyst. The molar ratio of the catalyst components Mo:Fe was 1:0.40.

2. Evaluation on Catalyst Activity

The activity and stability of the catalyst were tested in the same manner as in Example 1.

When the catalyst was used in the reaction at 270° C., the methanol conversion reached 98.5%, and the formaldehyde selectivity was 95.5%. After 240 hours of reaction, the methanol conversion was 91.6%, and the formaldehyde selectivity was 96.1%. The decrease of the methanol conversion was relatively large. The results are listed in Table 1.

Comparative Example 2

1. Preparation of Catalyst

The method for preparing the catalyst is similar to Example 1, except that phosphoric acid was not added:

88.28 grams of hexaammonium molybdate was dissolved in 500 grams of pure water to formulate solution A. 76.76 grams of ferric nitrate nonahydrate was dissolved in 400 grams of water, and then 9.38 grams of aluminum nitrate nonahydrate was added slowly to obtain solution B. Solution B was added dropwise to solution A slowly at 60° C. for 30 minutes under stirring. After the dropwise addition of solution B was completed, the resulting slurry was continued to be stirred at 80° C. for 2 hours for aging, and then dried at 150° C. for 12 hours. The dried material was pulverized to less than 200 mesh. Then, 2 grams of graphite and 10 grams of pure water were added and mixed uniformly, and then tabletting was performed. The tabletted sample was calcined at 450° C. for 6 h to obtain a catalyst. The molar ratio of the catalyst components Mo:Fe:Al was 1:0.38:0.1.

2. Evaluation on Catalyst Activity

The activity and stability of the catalyst were tested in the same manner as in Example 1.

When the catalyst was used in the reaction at 255° C., the methanol conversion reached 98.5%, and the formaldehyde selectivity was 94.8%. After 240 hours of reaction, the methanol conversion was 92.2%, and the formaldehyde selectivity was 95.0%. The decrease of the methanol conversion was relatively large. The results are listed in Table 1.

Comparative Example 3

1. Preparation of Catalyst

The method for preparing the catalyst is similar to Example 1, except that aluminum was not added:

88.28 grams of hexaammonium molybdate was dissolved in 500 grams of pure water to formulate solution A. 76.76 grams of ferric nitrate nonahydrate was dissolved in 400 grams of water, and then 5.90 grams of 83% phosphoric acid was added slowly to obtain solution B. Solution B was added dropwise to solution A slowly at 60° C. for 30 minutes under stirring. After the dropwise addition of solution B was completed, the resulting slurry was continued to be stirred at 80° C. for 2 hours for aging, and then dried at 150° C. for 12 hours. The dried material was pulverized to less than 200 mesh. Then, 2 grams of graphite and 10 grams of pure water were added and mixed uniformly, and then tabletting was performed. The tabletted sample was calcined at 450° C. for 6 h to obtain a catalyst. The molar ratio of the catalyst components Mo:Fe:P was 1:0.42:0.1.

2. Evaluation on Catalyst Activity

The activity and stability of the catalyst were tested in the same manner as in Example 1.

When the catalyst was used in the reaction at 268° C., the methanol conversion reached 98.5%, and the formaldehyde selectivity was 94.1%. After 240 hours of reaction, the methanol conversion was 93.1%, and the formaldehyde selectivity was 94.0%. The decrease of the methanol conversion was relatively large. The results are listed in Table 1.

Comparative Example 4

The method for preparing the catalyst is similar to Example 1, except that aluminum nitrate and phosphoric acid were not added:

88.28 grams of hexaammonium molybdate was dissolved in 500 grams of pure water to formulate solution A. 121.20 grams of ferric nitrate nonahydrate was dissolved in 400 grams of water to obtain solution B. Solution B was added dropwise to solution A slowly at 60° C. for 30 minutes under stirring. After the dropwise addition of solution B was completed, the resulting slurry was continued to be stirred at 80° C. for 2 hours for aging, and then dried at 150° C. for 12 hours. The dried material was pulverized to less than 200 mesh. Then, 2 grams of graphite and 10 grams of pure water were added and mixed uniformly, and then tabletted. The tabletted sample was calcined at 450° C. for 6 h to obtain a catalyst. The molar ratio of the catalyst components Mo:Fe was 1:0.6.

2. Evaluation on Catalyst Activity

The activity and stability of the catalyst were tested in the same manner as in Example 1.

When the catalyst was used in the reaction at 240° C., the methanol conversion reached 98.5%, and the formaldehyde selectivity was 91.2%. After 240 hours of reaction, the methanol conversion was 88.9%, and the formaldehyde selectivity was 89.0%. The decrease of the methanol conversion was relatively large. The results are listed in Table 1.

TABLE 1

| | Catalyst | Reaction Temperature, °C | Initial Activity Conversion | Initial Activity Selectivity | After 240 h Reaction Conversion | After 240 h Reaction Selectivity |
|---|---|---|---|---|---|---|
| Ex. 1 | $MoFe_{0.4}Al_{0.1}P_{0.3}O_x$ | 235 | 98.5% | 96.0% | 98.0% | 96.2% |
| Ex. 2 | $MoFe_{0.35}Al_{0.05}P_{0.15}O_x$ | 242 | 98.5% | 96.3% | 98.2% | 96.2% |
| Ex. 3 | $MoFe_{0.32}Al_{0.01}P_{0.03}O_x$ | 255 | 98.5% | 96.5% | 97.8% | 96.0% |
| Ex. 4 | $MoFe_{0.33}Al_{0.14}P_{0.40}O_x$ | 230 | 98.5% | 95.2% | 98.3% | 95.0% |
| Ex. 5 | $MoFe_{0.42}Al_{0.1}P_{0.1}O_x$ | 232 | 98.5% | 96.8% | 98.1% | 96.5% |
| Ex. 6 | $MoFe_{0.31}Al_{0.006}P_{0.006}O_x$ | 261 | 98.5% | 95.1% | 95.3% | 95.5% |
| Ex. 7 | $MoFe_{0.40}Al_{0.05}P_{0.1}O_x$ | 230 | 98.5% | 96.6% | 97.9% | 97.0% |
| Comp. Ex. 1 | $MoFe_{0.4}O_x$ | 270 | 98.5% | 95.5% | 91.6% | 96.1% |
| Comp. Ex. 2 | $MoFe_{0.38}Al_{0.1}O_x$ | 255 | 98.5% | 94.8% | 92.2% | 95.0% |
| Comp. Ex. 3 | $MoFe_{0.42}P_{0.1}O_x$ | 268 | 98.5% | 94.1% | 93.1% | 94.0% |
| Comp. Ex. 4 | $MoFe_{0.6}O_x$ | 240 | 98.5% | 91.2% | 88.9% | 89.0% |

As it can be seen from the above experimental results, the catalyst of the present invention has the advantages of low reaction temperature and stable catalyst performance.

What is claimed is:

1. A catalyst for selective oxidation of methanol to formaldehyde, wherein the catalyst has a general formula of $$MoFe_aAl_bP_cO_x$$

wherein a=0.25-0.5, b=0.001-0.2, c=0.001-0.6, and x is a number balancing the valence of the general formula.

2. The catalyst of claim 1, wherein
a=0.28-0.47;
b=0.003-0.018;
c=0.005-0.5;
x is a number balancing the valence of the general formula.

3. The catalyst of claim 1, wherein the catalyst is selected from $MoFe_{0.4}Al_{0.1}P_{0.3}O_x$, $MoFe_{0.35}Al_{0.05}P_{0.15}O_x$, $MoFe_{0.32}Al_{0.01}P_{0.03}O_x$, $MoFe_{0.33}Al_{0.14}P_{0.40}O_x$, $MoFe_{0.42}Al_{0.1}P_{0.1}O_x$, $MoFe_{0.31}Al_{0.006}P_{0.006}O_x$, $MoFe_{0.40}Al_{0.05}P_{0.1}O_x$, or a mixture of two or more thereof.

4. A method for preparing the catalyst of claim 1, wherein the method comprises:
providing an aqueous solution of a molybdenum salt with a molybdenum metal ion concentration of 0.1-2M in a stoichiometric amount;
formulating stoichiometric amounts of an iron salt, an aluminum salt and phosphoric acid into an aqueous solution with a total metal ion concentration of 0.1-5M;
mixing the above two solutions at 40-80° C. to obtain a slurry;
aging and drying the slurry, mixing with a solid lubricant and water, and then tabletting;
calcination.

5. The method of claim 4, wherein the method comprises adding the aqueous solution containing iron, aluminum and phosphoric acid to the aqueous solution of the molybdenum salt slowly at 40-80° C. to carry out preparation reaction.

6. The method of claim 5, wherein the precipitation reaction undergoes for a period of time of 30-120 minutes.

7. The method of claim 4, wherein the method further comprises a step of pulverizing a dried product obtained after the drying.

8. The method of claim 4, wherein the solid lubricant is selected from graphite, stearic acid or a mixture thereof.

9. The method of claim 4, wherein a tabletted product obtained after the tabletting is calcined at a temperature of 350° C.-500° C. for 2-12 hours.

10. A method comprising using the catalyst of claim 1 in selective oxidation of methanol to formaldehyde.

11. The catalyst of claim 1, wherein
a=0.36-0.38;
b=0.01-0.012;
c=0.02-0.2;
x is a number balancing the valence of the general formula.

12. The method of claim 5, wherein the precipitation reaction undergoes for a period of time of 70-80 minutes.

13. The method of claim 4, wherein a tabletted product obtained after the tabletting is calcined at a temperature of 420-440° C. for 6-8 hours.

\* \* \* \* \*